US011161820B2

(12) United States Patent
Yasukouchi et al.

(10) Patent No.: US 11,161,820 B2
(45) Date of Patent: Nov. 2, 2021

(54) PROCESS FOR PRODUCING ORGANIC COMPOUND

(71) Applicant: KANEKA CORPORATION, Osaka (JP)

(72) Inventors: Hiroaki Yasukouchi, Hyogo (JP); Akira Nishiyama, Hyogo (JP); Koji Machida, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 16/810,050

(22) Filed: Mar. 5, 2020

(65) Prior Publication Data

US 2020/0207717 A1 Jul. 2, 2020

Related U.S. Application Data

(63) Continuation of application No. PCT/JP2018/029556, filed on Aug. 7, 2018.

(30) Foreign Application Priority Data

Sep. 8, 2017 (JP) .............................. JP2017-173505

(51) Int. Cl.
*C07D 217/06* (2006.01)
*B01J 19/18* (2006.01)
*C01B 32/80* (2017.01)
*B01J 19/00* (2006.01)

(52) U.S. Cl.
CPC ........ *C07D 217/06* (2013.01); *B01J 19/0053* (2013.01); *B01J 19/1812* (2013.01); *C01B 32/80* (2017.08); *B01J 2219/00027* (2013.01)

(58) Field of Classification Search
CPC ............... B01J 19/1812; B01J 19/1818; B01J 19/2415; B01J 19/242; B01J 19/0053; B01J 2219/00027
See application file for complete search history.

(56) References Cited

FOREIGN PATENT DOCUMENTS

CN 101074193 A 11/2007

OTHER PUBLICATIONS

H. Eckert, "Phosgenation reactions with phosgene from triphosgene," Chimica Oggi/Chemistry Today, vol. 29, No. 6, pp. 40-46, Dec. 2011 (6 pages).

(Continued)

*Primary Examiner* — Lessanework Seifu
(74) *Attorney, Agent, or Firm* — Osha Bergman Watanabe & Burton LLP

(57) ABSTRACT

A process for producing an organic compound using a flow reactor for a first reaction in which a raw material liquid A and a raw material liquid B are mixed, and reacted in a reactor unit, and a flow reactor for a second reaction in which a first reaction solution discharged from the flow reactor for the first reaction and a raw material liquid C are mixed, and reacted in a reactor unit, wherein the raw material liquid A is a solution in which triphosgene and/or diphosgene is dissolved, wherein the raw material liquid B is a nitrogen-containing organic compound or a solution thereof, wherein the raw material liquid C is a reaction substrate having a functional group capable of reacting with phosgene, or a solution containing the reaction substrate, and wherein a product of the first reaction is phosgene.

6 Claims, 3 Drawing Sheets

(56) References Cited

OTHER PUBLICATIONS

S. Fuse et al., "Continuous in situ generation and reaction of phosgene in a microflow system," Chemical communications, vol. 47, pp. 12661-12663, Oct. 2011 (12 pages).

S. Fuse et al., "Efficient Amide Bond Formation through a Rapid and Strong Activation of Carboxylic Acids in a Microflow Reactor," Angewandte Chemie, International Edition, vol. 53, No. 3, pp. 851-855, 2014 (5 pages).

M. Irfan et al., "Continuous Flow Ozonolysis in a Laboratory Scale Reactor," Organic Letters, vol. 13, No. 5, pp. 984-987, 2011 (4 pages).

C.E. Brocklehurst et al., "Nitration Chemistry in Continuous Flow using Fuming Nitric Acid in a Commercially Available Flow Reactor," Organic Process Research & Development, vol. 15, No. 6, pp. 1447-1453, Apr. 29, 2011 (7 pages).

J. Pelleter et al., "Facile, Fast and Safe Process Development of Nitration and Bromination Reactions Using Continuous Flow Reactors," Organic Process Research & Development, vol. 13, No. 4, pp. 698-705, 2009 (8 pages).

H. Yasukouchi et al., "Safe and Efficient Phosgenation Reactions in a Continuous Flow Reactor," Organic Process Research & Development, vol. 22, pp. 247-251, Jan. 22, 2018 (5 pages).

International Search Report issued in corresponding International Application No. PCT/JP2018/029556; dated Nov. 13, 2018 (3 pages).

Written Opinion of the International Searching Authority issued in corresponding International Application No. PCT/JP2018/029556; dated Nov. 13, 2018 (4 pages).

Extended European Search Report issued in the counterpart European Patent Application No. 18853393.9, dated Jan. 22, 2021 (6 pages).

Ortar Giorgio et al.; "Biaryl tetrazolyl ureas as inhibitors of endocannabinoid metabolism: Modulation at the N-portion and distal phenyl ring", European Journal of Medicinal Chemistry, Elsevier, Amsterdam, NL, vol. 63, Feb. 15, 2013, pp. 118-132, XP029233967 (15 pages).

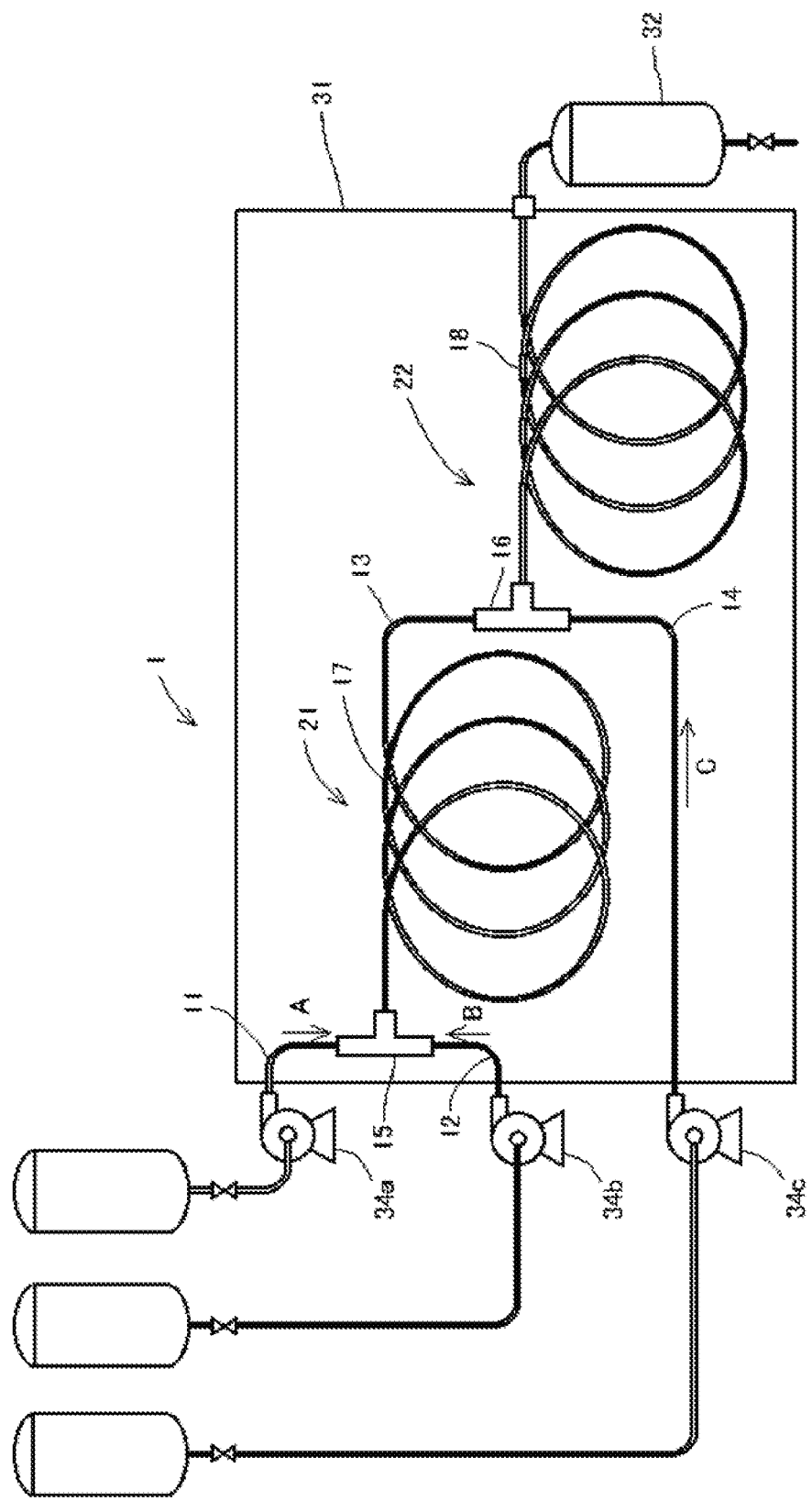
[FIG. 1]

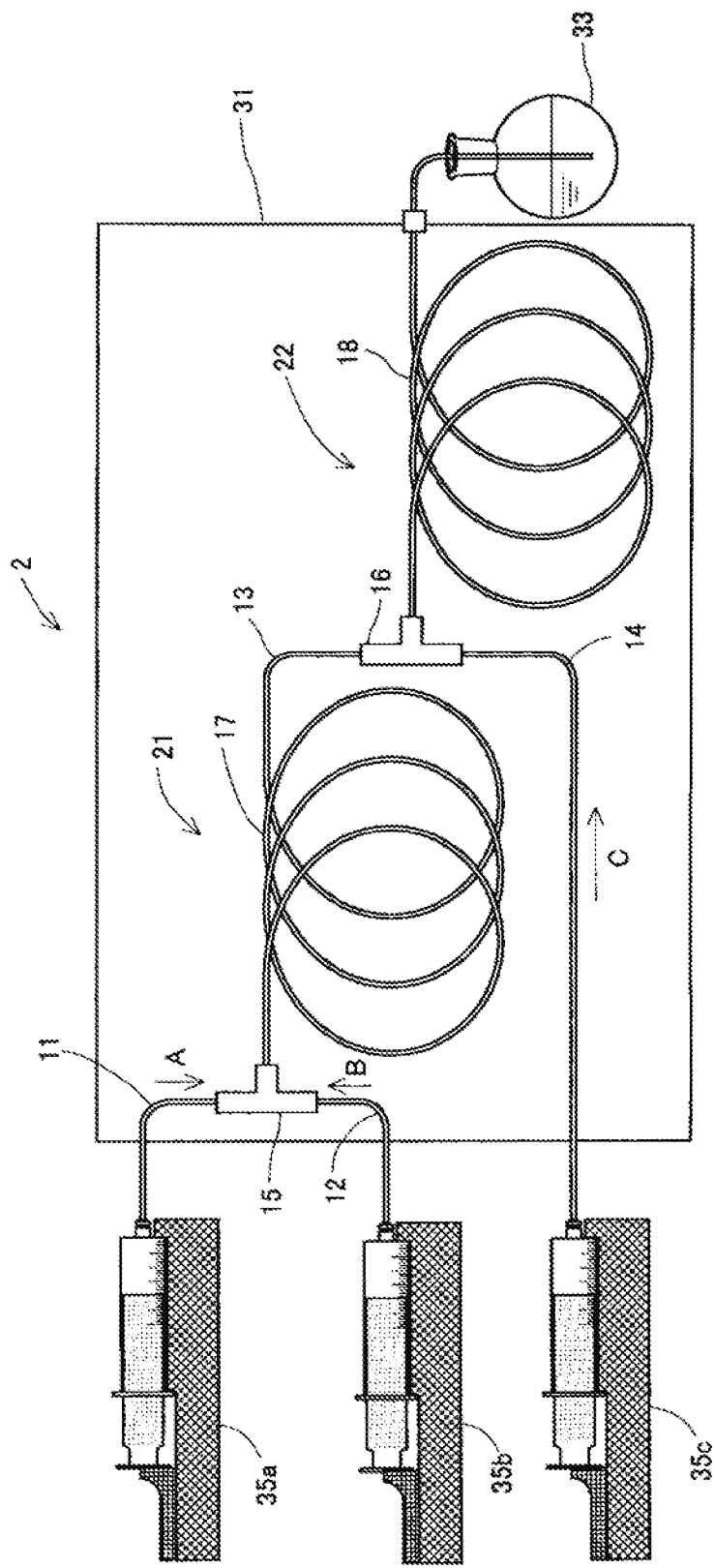
[FIG. 2]

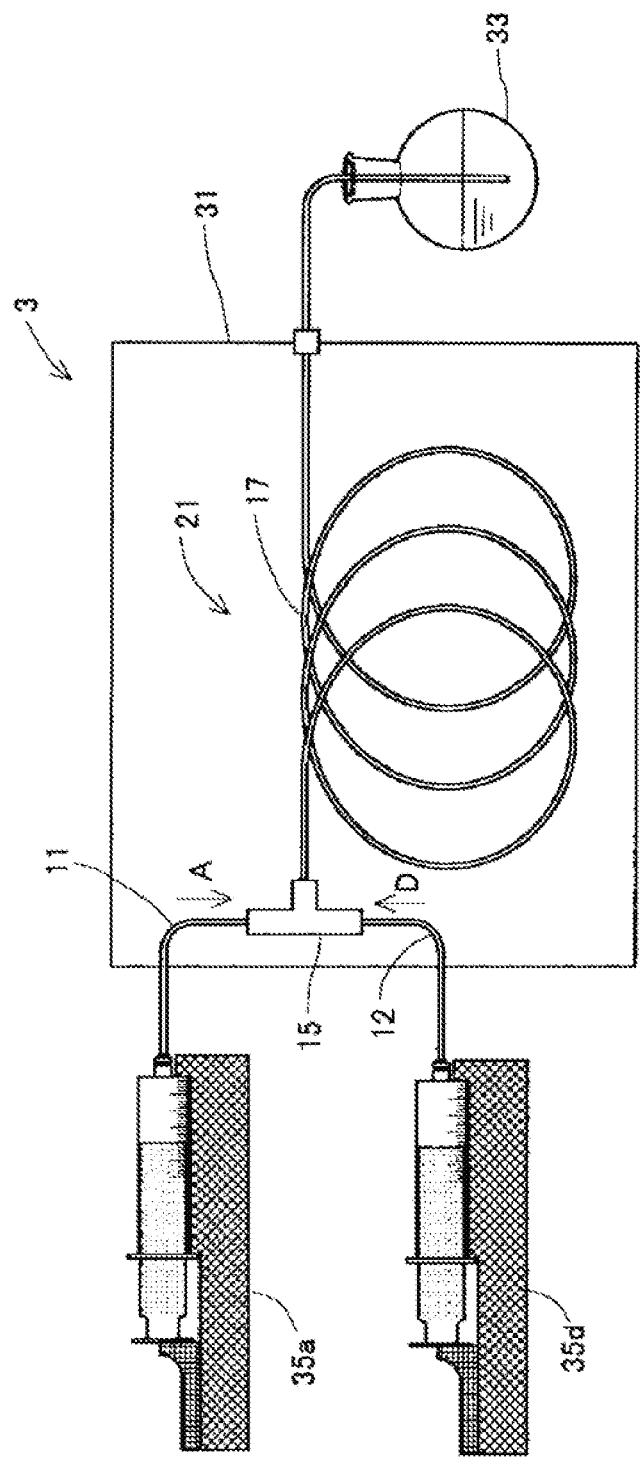
[FIG. 3]

PROCESS FOR PRODUCING ORGANIC COMPOUND

This application is a continuation claiming priority to PCT/JP2018/029556, published as WO2019/049584 and filed on Aug. 7, 2018, which claims priority to Japan Patent Application Serial No. JP2017-173505, filed on Sep. 8, 2017.

TECHNICAL FIELD

One or more embodiments of the present invention relate to a process for producing an organic compound in a flow reactor using a phosgene alternative reagent.

BACKGROUND

Phosgene is used as a reagent for various organic synthesis reactions because of its high reactivity, and is used for, for example, being allowed to react with a compound having a hetero atom, such as alcohol, thiol, amine, carboxylic acid, or the like, to perform carbonylation (including chlorocarbonylation) of the compound. Since phosgene is a highly toxic gas and difficult to handle, a phosgene alternative reagent such as diphosgene and triphosgene may be used. It is known that a phosgene alternative reagent generates phosgene by reacting with an amine.

Non-Patent Documents 1 and 2 describe that using of a microflow system with use of triphosgene makes it possible to minimize a reactor and thus to further enhance safety. Specifically, Non-Patent Documents 1 and 2 describe that a solution in which a certain N-protected amino acid and diisopropylamine are dissolved in a methylene chloride and a solution in which triphosgene is dissolved are mixed with a T-shape mixer, and the resultant mixture is passed through a reaction tube, whereby phosgene is generated from triphosgene in the mixer and the reaction tube and is immediately reacted with the N-protected amino acid in situ to produce an appropriate acid chloride.

CITATION LIST

Non-Patent Literature

Non-Patent Document 1: Fuse et al, Chem. Commun., 2011, 47, 12661-12663
Non-Patent Document 2: Fuse et al, Angew. Chem. Int. Ed., 2014, 53, 851-855

However, in a reaction in a microflow system using a phosgene alternative reagent such as diphosgene or triphosgene as a raw material, there is room for further improvement in the reaction yield.

One or more embodiments of the present invention has been made by focusing on the above situation, and an object of one or more embodiments of the present invention is to further enhance a product yield when a phosgene alternative reagent is used in a flow reactor.

SUMMARY

As a result of intensive studies, the inventors have devised a combination of flow reactors and found that a phosgene alternative reagent such as diphosgene or triphosgene is first reacted with a nitrogen-containing organic compound in a first flow reactor to prepare phosgene, and the resulting phosgene is reacted with a reaction substrate in a second flow reactor, whereby generation of impurities by a side reaction is suppressed, and the product yield is significantly improved. One or more embodiments of the present invention have been achieved based on such findings.

That is, one or more embodiments of the present invention are as follows:

[1] A process for producing an organic compound using
a flow reactor for a first reaction in which a raw material liquid A and a raw material liquid B are introduced from separate feeding channels, mixed in a mixing unit, and then reacted in a reactor unit, and
a flow reactor for a second reaction in which a first reaction solution discharged from the flow reactor for the first reaction and a raw material liquid C are introduced from separate feeding channels, mixed in a mixing unit, and then reacted in a reactor unit,
wherein the raw material liquid A is a solution in which triphosgene and/or diphosgene is dissolved,
wherein the raw material liquid B is a nitrogen-containing organic compound not including an amino group optionally having one substituent on N, an amido group optionally having one substituent on N, and —OC(=O)NH$_2$ optionally having one substituent on N, or a solution of the nitrogen-containing organic compound,
wherein the raw material liquid C is a reaction substrate having at least one functional group capable of reacting with phosgene, the functional group being selected from the group consisting of an amino group optionally having one substituent on N, an amido group optionally having one substituent on N, and —OC(=O)NH$_2$ optionally having one substituent on N, or a solution containing the reaction substrate, and
wherein a product of the first reaction is phosgene.

[2] The process according to the above [1],
wherein the organic compound produced is a compound having at least one functional group selected from the group consisting of a chlorocarbonylated amino group optionally having one substituent on N, a chlorocarbonylated amide group optionally having one substituent on N, and a chlorocarbonylated —OC(=O)NH$_2$ group optionally having one substituent on N, a compound having a structure of N-carboxyanhydride (NCA), or a compound having a isocyanate or urea structure.

[3] The process according to the above [1] or [2],
wherein the nitrogen-containing organic compound not including an amino group optionally having one substituent on N, an amido group optionally having one substituent on N, and —OC(=O)NH$_2$ optionally having one substituent on N is a trialkylamine having 9 to 40 carbon atoms, and
wherein the solution in which triphosgene and/or diphosgene is dissolved contains an organic solvent.

[4] The process according to any of the above [1] to [3],
wherein a flow channel to discharge the first reaction solution from the reactor unit of the flow reactor for the first reaction is directly connected to the mixing unit of the flow reactor for the second reaction.

[5] The process according to any of the above [1] to [4],
wherein the reactor unit has a cross-sectional area of 0.15 mm$^2$ or more and 30 cm$^2$ or less.

According to one or more embodiments of the present invention, when a phosgene alternative reagent such as diphosgene or triphosgene is used in a flow reactor, generation of impurities by a side reaction can be suppressed, and a product yield can be significantly enhanced.

BRIEF DESCRIPTION OF THE DRAWINGS

FIG. 1 is a schematic view showing one example of a flow reactor of one or more embodiments of the present invention.

FIG. 2 is a schematic view showing another example of a flow reactor of one or more embodiments of the present invention.

FIG. 3 is a schematic view showing another example of a flow reactor in one or more embodiments of the Reference Examples and Comparative Examples.

DETAILED DESCRIPTION OF EMBODIMENTS

One or more embodiments of the present invention relate to a process for producing an organic compound in a flow reactor using a phosgene alternative reagent (synthetic equivalent of phosgene). The flow reactor includes both a chemical reaction apparatus (micro-flow reactor) utilizing a microchannel in the order of submillimeter and a scaled-up apparatus of the micro-flow reactor. The micro-flow reactor has specific effects, due to the micro reaction field, such as high-speed mixing performance (for example, when two liquids are mixed in a micro-space, the substance diffusion distance in the two liquids decreases, resulting in shortening the time of mass transfer movement), heat removal efficiency (since the reaction field is small, thermal efficiency is extremely high and temperature control is easy), reaction control performance, interface control performance, or the like. In addition, the micro-flow reactor can improve safety and reduce the cost of equipment along with downsizing of the process, process intensification (micro in macro) by incorporating into existing processes, and production of substances that may not be produced by an existing production method. On the other hand, a limited amount can be processed with the micro flow reactor at one time. The flow reactor also includes a chemical reaction apparatus in which the diameter of a flow channel is enlarged to the order of millimeters to centimeters to the extent that the characteristics of the micro-flow reactor are not impaired, thereby improving operability. Therefore, the flow reactor can be practically used because a processing amount can be increased. Specifically, the flow reactor is composed of two or more feeding channels (which may be feeding lines and may be identified as "raw material feeding ports"), a mixing unit to mix fed raw materials, and a reactor unit in which a mixed solution flows (which is also called a reactor channel or a retention channel, and may be a reactor line or a retention line).

FIG. 1 is a schematic view showing a reaction apparatus 1 using the above-mentioned flow reactor, which is adopted in one or more embodiments of the present invention. The reaction apparatus 1 is composed of;

a flow reactor 21 for a first reaction having two feeding channels 11 and 12 to introduce a raw material liquid A and a raw material liquid B separately, a first mixing unit 15 to mix the raw material liquids A and B fed from the respective feeding channels 11 and 12, and a first reactor unit 17 to react a mixed solution prepared in the mixing unit; and a flow reactor 22 for a second reaction having two feeding channels 13 and 14 to introduce a first reaction solution discharged from the flow reactor for the first reaction and a raw material liquid C separately, a second mixing unit 16 to mix the first reaction solution and the raw material liquid C fed from the respective feeding channels 13 and 14, and a second reactor unit 18 to react a mixed solution prepared in the mixing unit. The flow channel 13 to discharge the first reaction solution from the reactor unit 17 of the flow reactor 21 for the first reaction also serves as the feeding channel 13 of the flow reactor 22 for the second reaction, and this discharge channel 13 is directly connected to the mixing unit 16. The use of such two flow reactors 21 and 22 allows the two reactions, including the first and second reactions.

In one or more embodiments of the present invention, as the raw material liquid A in the flow reactor 21 for the first reaction, a solution in which a phosgene alternative reagent (that is, triphosgene and/or diphosgene) is dissolved is used. As the raw material liquid B in the flow reactor 21 for the first reaction, a nitrogen-containing organic compound not including an amino group optionally having one substituent on N (hereinafter, unless otherwise indicated, the "amino group" means not only an unsubstituted amino group but also an amino group having one substituent on N, and the amino group having one substituent on N may be referred to as an N-monosubstituted amino group), an amido group optionally having one substituent on N (hereinafter, unless otherwise indicated, the "amide group" means not only an unsubstituted amide group but also an amide group having one substituent on N), and —OC(=O)NH$_2$ optionally having one substituent on N (hereinafter referred to as an "—OC(=O)NH$_2$ group") or a solution of the nitrogen-containing organic compound is used. A solution containing phosgene (first reaction solution) is obtained as a product of the first reaction. In the subsequent flow reactor 22 for the second reaction, as a raw material liquid C, a reaction substrate having at least one functional group capable of reacting with phosgene (hereinafter sometimes referred to as a reactive group with phosgene or simply a reactive group) that is selected from the group consisting of an amino group (an amino group optionally having one substituent on N, as defined above), an amide group (an amide group optionally having one substituent on N, as defined above), and an —OC(=O)NH$_2$ group, or a solution containing the reaction substrate is used. This reaction substrate or the solution is reacted with the first reaction solution (phosgene-containing solution) to produce an organic compound (hereinafter sometimes referred to as a desired organic compound or a product). Thus, in one or more embodiments of the present invention, phosgene is first generated in the first flow reactor 21, and then the reaction substrate having a reactive group with phosgene and the phosgene above generated are reacted in another reaction field in the second flow reactor 22, whereby the yield of a desired organic compound is remarkably improved. On the other hand, as in Non-Patent Documents 1 and 2, when a solution containing a reaction substrate and an amine and a solution containing triphosgene are reacted in a single reaction field in a conventional flow reactor, the reaction yield may not be improved sufficiently. The reason therefore is assumed to be as follows: 1) before phosgene is formed from triphosgene, an impurity (hereinafter may be referred to as a by-product) is produced due to a side reaction of triphosgene or diphosgene with the reaction substrate, and 2) since the produced impurity is relatively stable, it does not undergo decomposition (phosgenation) and remains even in the presence of amines. By adopting the method of one or more embodiments of the present invention, since the reaction substrate is reacted after sufficiently forming phosgene from triphosgene, the production of impurity due to the above side reaction can be sufficiently suppressed, and hence the yield of the desired organic compound is improved.

In one or more embodiments, when the reactive group with phosgene contained in the reaction substrate to be used as the raw material liquid C in the second flow reactor 22 is reacted with phosgene at a ratio of 1:1 (molar ratio), the amount of the phosgene alternative reagent contained in the raw material liquid A in the first flow reactor 21 is, for example, 0.2 equivalents or more, 0.5 equivalents or more, or 0.8 equivalents or more, and is, for example, 3 equivalents or less, 2 equivalents or less, or 1.5 equivalents or less, relative to 1 mol of the reactive group. When the above reactive group and phosgene are reacted at a ratio of 2:1 (molar ratio), the amount of the phosgene alternative reagent is, for example, 0.4 equivalents or more, 0.5 equivalents or more, or 0.55 equivalents or more, and is, for example, 1 equivalent or less, 0.75 equivalents or less, or 0.65 equivalents or less, relative to 1 mol of the reactive group. Note that 1 mol of triphosgene corresponds to 3 equivalents relative to 1 mol of the reactive group with phosgene. 1 mol of diphosgene corresponds to 2 equivalents relative to 1 mol of the reactive group with phosgene.

In one or more embodiments, the raw material liquid A may be prepared by dissolving the phosgene alternative reagent in an organic solvent. Examples of the organic solvent include an aliphatic hydrocarbon solvent such as n-hexane, cyclohexane, and methylcyclohexane; an aromatic hydrocarbon solvent such as benzene, toluene, and xylene; an ether solvent such as diethyl ether, diisopropyl ether, tetrahydrofuran, 2-methyltetrahydrofuran, 4-methyltetrahydropyran, tert-butyl methyl ether, 1,4-dioxane, and cyclopentyl methyl ether; a halogen-containing solvent such as dichloromethane, chloroform, 1,1,1-trichloroethane, and chlorobenzene; an ester solvent such as ethyl acetate, propyl acetate, and butyl acetate; a ketone solvent such as acetone, methyl ethyl ketone, and methyl isobutyl ketone; a nitrile solvent such as acetonitrile, propionitrile, and butyronitrile; and an amide solvent such as N,N-dimethylformamide, N,N-dimethylacetamide, and N-methylpyrrolidone. These solvents may be used alone or in combination of two or more kinds, and there is no restriction on the mixing ratio thereof.

In one or more embodiments of the present invention, from the viewpoints of reactivity, post-treatment, and the like, an aromatic hydrocarbon solvent, an ether solvent, and a nitrile solvent may be used. Toluene, tetrahydrofuran, and acetonitrile may also be used. In some solvents, hydrochloride of a nitrogen-containing organic compound described later may have low solubility. However, by appropriately selecting a nitrogen-containing organic compound, the precipitation of hydrochloride can be prevented.

In one or more embodiments, the amount of the organic solvent in the raw material liquid A containing the phosgene alternative reagent is, for example, 0.1 parts by weight or more, 0.5 parts by weight or more, and.0 part by weight or more, and is, for example, 100 parts by weight or less, 50 parts by weight or less, 30 parts by weight or less, or 10 parts by weight or less, relative to 1 part by weight of the phosgene alternative reagent.

As the nitrogen-containing organic compound to be used as the raw material liquid B in the first flow reactor 21, a nitrogen-containing organic compound having no reactive group with phosgene, such as an amino group, an amide group, and an —OC(=O)NH$_2$ group, can be used. Examples of the nitrogen-containing organic compound include trimethylamine, triethylamine, tripropylamine, tributylamine, tripentylamine, trihexylamine, triheptylamine, trioctylamine, tridodecylamine, dodecyldimethylamine, hexyldibutylamine, diisopropylbutylamine, diethylamine, diisopropylethylamine, dimethylethylamine, dicyclohexylmethylamine, N-methylpyrrolidine, N-methylmorpholine, 1,8-diazabicyclo[5,4,0]undec-7-ene, pyridine, 2-picoline, 3-picoline, 2,6-lutidine, collidine, 4-dimethylaminopyridine, quinoline, imidazole, N-methylimidazole and the like. These nitrogen-containing organic compounds may be used singly or in combination of two or more kinds. When using in combination of two or more kinds, there are no restrictions on the mixing ratio. The tertiary amine such as tripropylamine, tributylamine, trihexylamine, trioctylamine, diisopropylethylamine, 1,8-diazabicyclo[5,4,0]undec-7-ene, N-methylimidazole, or the like may be used, and a trialkylamine such as tripropylamine, tributylamine, trihexylamine, trioctylamine, or diisopropylethylamine may be used.

In one or more embodiments, the trialkylamine can be a trialkylamine having 9 to 40 carbon atoms. In this reaction, since the nitrogen-containing organic compound forms hydrochloric acid and hydrochloride generated when the reaction substrate reacts with phosgene, there is a risk of clogging of a flow channel during a flow reaction due to the precipitation of the salt. However, when a trialkylamine having 9 to 40 carbon atoms is used as the nitrogen-containing organic compound, the generated hydrochloride has high solubility, and clogging of a flow channel of a flow reactor can be prevented. From the viewpoint of increasing the solubility of hydrochloride, the trialkylamine can be a noncyclic trialkylamine. The number of carbon atoms of the trialkylamine may be 9 or more or 12 or more, and may be 40 or less, 30 or less, or 24 or less.

Examples of a noncyclic trialkylamine having 9 to 40 carbon atoms include tripropylamine, tributylamine, tripentylamine, trihexylamine, triheptylamine, trioctylamine, tridodecylamine, dodecyldimethylamine, hexyldibutylamine, and diisopropylbutylamine. From the viewpoint of availability, tripropylamine, tributylamine, trihexylamine, and trioctylamine can be used, and tributylamine can be used.

Since the nitrogen-containing organic compound serves as a catalyst, the amount of the nitrogen-containing organic compound used may be small. The number of moles of nitrogen atoms in the nitrogen-containing organic compound is, for example 0.5 mol or more, 1 mol or more, 2 mol or more, 2.5 mol or more, or 3 mol or more, relative to 1 mol of triphosgene. The upper limit amount of the nitrogen-containing organic compound used is not particularly limited. However, the amount of nitrogen atoms in the nitrogen-containing organic compound may be, for example, 8 mol or less, 6 mol or less, or 4 mol or less, relative to 1 mol of triphosgene.

In addition, the amount of nitrogen atoms in the nitrogen-containing organic compound is, for example, 0.5 mol or more, 1 mol or more, 1.5 mol or more, 1.8 mol or more, or 2 mol or more, relative to 1 mol of diphosgene. The upper limit amount of the nitrogen-containing organic compound used is not particularly limited. However, the amount of nitrogen atoms in the nitrogen-containing organic compound may be, for example, 15 mol or less, 10 mol or less, or 5 mol or less, relative to 1 mol of diphosgene.

Part of the nitrogen-containing organic compound may be contained in the raw material liquid C. When the nitrogen-containing organic compound is contained in both the raw material liquid B and the raw material liquid C, the using amount of the nitrogen-containing organic compound means the total using amount of the nitrogen-containing organic compounds in the raw material liquid B and the raw material liquid C.

The nitrogen-containing organic compound may be used as the raw material liquid B in a solvent-free state when used at a temperature equal to or higher than a melting point. However, if necessary, a solution in which the nitrogen-containing organic compound and an organic solvent coexist may be used as the raw material liquid B. The organic solvent can be selected from the same range as the solvents that can be used in the raw material liquid A containing the phosgene alternative reagent.

The amount of the organic solvent in the raw material liquid B is, for example, 1 part by mass or more, 10 parts by mass or more, or 30 parts by mass or more, and is, for example, 10000 parts by mass or less, 5000 parts by mass or less, or 3000 parts by mass or less, relative to 100 parts by mass of the nitrogen-containing organic compound.

A time (reaction time, retention time) during which the mixed solution of the raw material liquid A (phosgene alternative reagent) and the raw material liquid B (nitrogen-containing organic compound) flows in the reactor unit 17 of the first flow reactor 21 may be appropriately set according to the types of the raw material liquids A and B and the flow velocities at which the raw material liquids A and B are flowed in the flow channels, and is, for example, 0.5 seconds or more, 0.7 seconds or more, more 0.8 seconds or more, or 1.0 second or more, and is, for example, 15 minutes or less, 10 minutes or less, or 5 minutes or less.

The flow velocities at which the raw material liquid A and the raw material liquid B flow in the feeding channels 11 and 12, respectively, and the flow velocity at which the mixed solution of the raw material liquid A and the raw material liquid B flows in the reactor unit 17 of the first flow reactor 21 may be appropriately set according to the types of the raw material liquids A and B and a retention time in the reactor unit 17. Each flow velocity is, for example, 0.01 mL/min or more, 0.1 mL/min or more, or 0.5 mL/min or more, and is, for example, 5000 mL/min or less, 3000 mL/min or less, or 1000 mL/min (60 L/hour) or less.

In the reaction apparatus 1, a device (temperature control room, temperature control bath, jacket container, etc.; temperature control bath in the illustrated example) 31 to control the temperatures of the reactor units 17 and 18 may be provided independently in each the reactor unit or common to all the reactor units. The reaction temperature (set temperature of the temperature control device 31) of the raw material liquid A (phosgene alternative reagent) and the raw material liquid B (nitrogen-containing organic compound) is, for example, −50° C. or higher, −30° C. or higher, or −10° C. or higher, and is, for example, 100° C. or lower, 50° C. or lower, or 25° C. or lower.

The phosgene prepared in the first flow reactor 21 is fed to the second flow reactor 22 through the feeding channel 13 and mixed with a reaction substrate contained in the raw material liquid C in the mixing unit 16 of the reactor 22.

As described above, the reaction substrate has a reactive group with phosgene such as an amino group, an amide group, and an —OC(=O)NH$_2$ group. The number of the reactive groups may be one or more, and may be two, three, or four or more, per one molecule of the substrate, but may be 1 to 4, 1 to 3, or 1 or 2. When a plurality of reactive groups are contained, the reactive groups may be the same or different.

As the reaction substrate, the compounds represented by the following formulae (1) to (3) can be used:

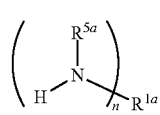
(1)

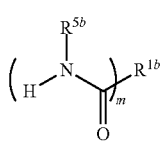
(2)

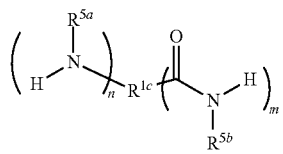
(3)

wherein $R^{1a}$, $R^{1b}$, and $R^{1c}$ each represent a portion other than the reactive group with phosgene of the reaction substrate; $R^{5a}$ and $R^{5b}$ each represent a hydrogen atom or an organic group (having no reactive group with phosgene); $R^{1a}$ or $R^{1c}$ and $R^{5a}$ may be bonded to each other; $R^{1b}$ or $R^{1c}$ and $R^{5b}$ may be bonded to each other; when a plurality of $R^{5a}$'s and a plurality of $R^{5b}$'s are present, $R^{5a}$'s and $R^{5b}$'s may be the same or different; and n and m each represent an integer of 1 to 3; the sum of n and m is 1 to 3, or 1 or 2.

$R^{1a}$ to $R^{1c}$ and $R^{5a}$ to $R^{5b}$ can have various complicated structures according to the reaction substrate, but may have a simple structure.

Examples of $R^{5a}$ and $R^{5b}$ having a simple structure include a hydrogen atom, an alkyl group having 1 to 20 carbon atoms and optionally having a substituent, an alkenyl group having 2 to 20 carbon atoms and optionally having a substituent, a cycloalkyl group having 3 to 20 carbon atoms and optionally having a substituent, an aralkyl group having 7 to 20 carbon atoms and optionally having a substituent, an aryl group having 6 to 20 carbon atoms and optionally having a substituent, a heteroaryl group having 3 to 20 carbon atoms and optionally having a substituent, an alkoxy group having 1 to 20 carbon atoms and optionally having a substituent, an aralkyloxy group having 7 to 20 carbon atoms and optionally having a substituent, an aryloxy group having 6 to 20 carbon atoms and optionally having a substituent, and a group in which a hydrogen atom is removed from each of the above-mentioned groups to form a bond with $R^{1a}$, $R^{1b}$, or $R^{1c}$.

The alkyl group serving as $R^{5a}$ and $R^{5b}$ may be a group having 1 to 10 carbon atoms such as a methyl group, an ethyl group, a propyl group, a butyl group, a pentyl group, or a hexyl group, and can be a group having 1 to 4 carbon atoms.

The alkenyl group serving as $R^{5a}$ and $R^{5b}$ may be a group having 2 to 10 carbon atoms such as an ethenyl group, a propenyl group, a butenyl group, a pentenyl group, or a hexenyl group, and can be a group having 2 to 4 carbon atoms.

The cycloalkyl group serving as $R^{5a}$ and $R^{5b}$ may be a group having 3 to 10 carbon atoms such as a cyclopropyl group, a cyclobutyl group, a cyclopentyl group, or a cyclohexyl group, and can be a group having 5 to 6 carbon atoms.

The aralkyl group serving as $R^{5a}$ and $R^{5b}$ may be a group having 7 to 15 carbon atoms such as a benzyl group, a phenethyl group, or a phenylpropyl group, and can be a group having 7 to 10 carbon atoms.

The aryl group serving as $R^{5a}$ and $R^{5b}$ may be a group having 6 to 10 carbon atoms such as a phenyl group, a toluyl group, or a naphthyl group, and can be a group having 6 to 8 carbon atoms.

Examples of the heteroaryl group serving as $R^{5a}$ and $R^{5b}$ include a pyridinyl group, a pyrazinyl group, a pyrimidinyl group, and a pyridazinyl group.

The alkoxy group serving as $R^{5a}$ and $R^{5b}$ may be a group having 1 to 10 carbon atoms such as a methoxy group, an ethoxy group, a propoxy group, or a butoxy group, and can be a group having 1 to 4 carbon atoms.

The aralkyloxy group serving as $R^{5a}$ and $R^{5b}$ may be a group having 7 to 15 carbon atoms such as a benzyloxy group or a phenethyloxy group, and can be a group having 7 to 10 carbon atoms.

The aryloxy group serving as $R^{5a}$ and $R^{5b}$ may be a group having 6 to 10 carbon atoms such as a phenyloxy group or a naphthyloxy group, and can be a group having 6 to 8 carbon atoms.

Examples of the substituent that $R^{5a}$ and $R^{5b}$ may have include fluorine atom; an alkoxy group such as a methoxy group, an ethoxy group, a phenoxy group, or a benzyloxy group; a cyclic ether group such as an epoxy group; an alkylthio group such as a methylthio group; a trifluoromethyl group; an acetyl group; a benzoyl group; a cyano group; a nitro group; an alkoxycarbonyl group such as a methoxycarbonyl group or an ethoxycarbonyl group; a dialkylamino group such as a dimethylamino group, a diethylamino group, or a pyrrolidyl group; and a protected amino group such as a benzyloxycarbonylamino group, a tert-butylcarbonylamino group, an acetylamino group, or a benzoylamino group. The substituent may be one other than a reactive group with phosgene. Further, the substituent may be a divalent group, and includes, for example, —$CH_2$—O—. When two bonds of —$CH_2$—O— are bonded to the same carbon atom, an oxirane ring is formed. There is no restriction on the number of the substituents.

Examples of $R^{1a}$ to $R^{1c}$ having a simple structure include an alkyl group having 1 to 20 carbon atoms and optionally having a substituent or a divalent or trivalent group obtained by removing one or two hydrogen atoms from the alkyl group (hereinafter, these may be collectively referred to as alkyl-derived groups); an alkenyl group having 2 to 20 carbon atoms and optionally having a substituent or a divalent or trivalent group obtained by removing one or two hydrogen atoms from the alkenyl group (hereinafter, these may be collectively referred to as alkenyl-derived groups); a cycloalkyl group having 3 to 20 carbon atoms and optionally having a substituent or a divalent or trivalent group obtained by removing one or two hydrogen atoms from the cycloalkyl group (hereinafter, these may be collectively referred to as cycloalkyl-derived groups); an aralkyl group having 7 to 20 carbon atoms and optionally having a substituent or a divalent or trivalent group obtained by removing one or two hydrogen atoms from the aralkyl group (hereinafter, these may be collectively referred to as aralkyl-derived groups); an aryl group having 6 to 20 carbon atoms and optionally having a substituent or a divalent or trivalent group obtained by removing one or two hydrogen atoms from the aryl group (hereinafter, these may be collectively referred to as aryl-derived groups); and a heteroaryl group having 3 to 20 carbon atoms and optionally having a substituent or a divalent or trivalent group obtained by removing one or two hydrogen atoms from the heteroaryl group (hereinafter, these may be collectively referred to as heteroaryl-derived groups). Each of $R^{1b}$ and $R^{1c}$ may be a group in which an oxy group (—O—) is bonded to any of the alkyl-derived groups, the alkenyl-derived groups, the cycloalkyl-derived groups, the aralkyl-derived groups, the aryl-derived groups, or the heteroaryl-derived groups. The oxy group also bonds to —C(=O)$NR^{5b}$H represented by the formula (2) or (3).

Examples of the alkyl group, the alkenyl group, the cycloalkyl group, the aralkyl group, the aryl group, and the heteroaryl group serving as $R^{1a}$ to $R^{1c}$ include the same groups as those exemplified for $R^{5a}$ and $R^{5b}$. Further, examples of the substituents of $R^{1a}$ to $R^{1c}$ include the same substituents as those exemplified for $R^{5a}$ and $R^{5b}$.

$R^{1a}$ or $R^{1c}$ and $R^{5a}$, or $R^{1b}$ or $R^{1c}$ and $R^{5b}$ may be bonded to each other to form a ring containing at least one or more (including 5 or less, or 2 or less) nitrogen atoms as the constituent elements of the ring. The ring formed by bonding $R^{1a}$ or $R^{1c}$ and $R^{5a}$, or $R^{1b}$ or $R^{1c}$ and $R^{5b}$ to each other has 2 or more, or 4 or more, or 0 or less, or 20 or less carbon atoms. The ring formed by bonding $R^{1a}$ or $R^{1c}$ and $R^{5a}$, or $R^{1b}$ or $R^{1c}$ and $R^{5b}$ to each other can be a monocyclic system, a bicyclic system, or a tricyclic system.

The ring formed by bonding $R^{5a}$ or $R^{1c}$ and $R^{5a}$, or $R^{1b}$ or $R^{1c}$ and $R^{5b}$ to each other may have a substituent, and examples of the substituent include an alkyl group having 1 to 20 carbon atoms and optionally having a substituent, an alkenyl group having 2 to 20 carbon atoms and optionally having a substituent, a cycloalkyl group having 3 to 20 carbon atoms and optionally having a substituent, an aralkyl group having 7 to 20 carbon atoms and optionally having a substituent, an aryl group having 6 to 20 carbon atoms and optionally having a substituent, a heteroaryl group having 3 to 20 carbon atoms and optionally having a substituent, an alkoxy group having 1 to 20 carbon atoms and optionally having a substituent, an aralkyloxy group having 7 to 20 carbon atoms and optionally having a substituent, an aryloxy group having 6 to 20 carbon atoms and optionally having a substituent, and a substituent that the group as $R^{5a}$ or $R^{5b}$ may have. The substituent can be an aryl group having 6 to 20 carbon atoms and optionally having a substituent, and a specific group can appropriately refer to $R^{5a}$ or $R^{5b}$. The number of the substituents is not particularly limited.

When the reaction substrate has "$R^{5a}$—N—$R^{1a}$" or "$R^{5a}$—N—$R^{1c}$" in the structural formula as in the formula (1) or (3), $R^{1a}$ or $R^{1a}$ or $R^{1c}$ and $R^{5a}$ are bonded to each other (for example, formally, a hydrogen atom is removed from $R^{1a}$ or $R^{1c}$ and a hydrogen atom is removed from $R^{5}$a to form a bond) to form a ring containing at least one or more (including 5 or less, or 2 or less) nitrogen atoms as the constituent elements of the ring. Examples of the ring formed by bonding $R^{1a}$ or $R^{1c}$ and $R^{5a}$ to each other include the following rings.

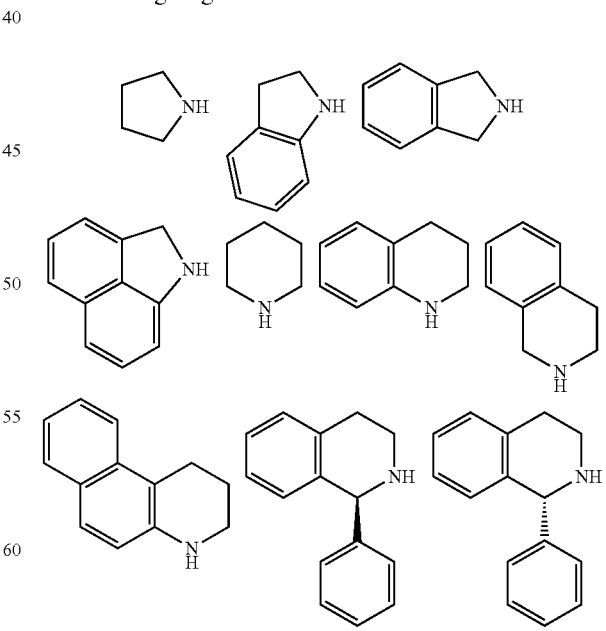

On the other hand, when the reaction substrate has "$R^{5b}$—NH—C(=O)—$R^{1b}$" or "$R^{5b}$—NH—C(=O)—$R^{1c}$" in the structural formula as in the formula (2) or (3), $R^{1b}$ or $R^{1c}$ and $R^{5b}$ are bonded to each other (for example, formally, a hydrogen atom is removed from $R^{1b}$ or $R^{1c}$ and a hydrogen atom is removed from $R^{5b}$ to form a bond) to form a ring containing at least one or more (including 5 or less, or 2 or less) —NH—C(=O)— groups as the constituent elements of the ring. Examples of the ring formed by bonding $R^{1b}$ or $R^{1c}$ and $R^{5b}$ to each other include the following rings.

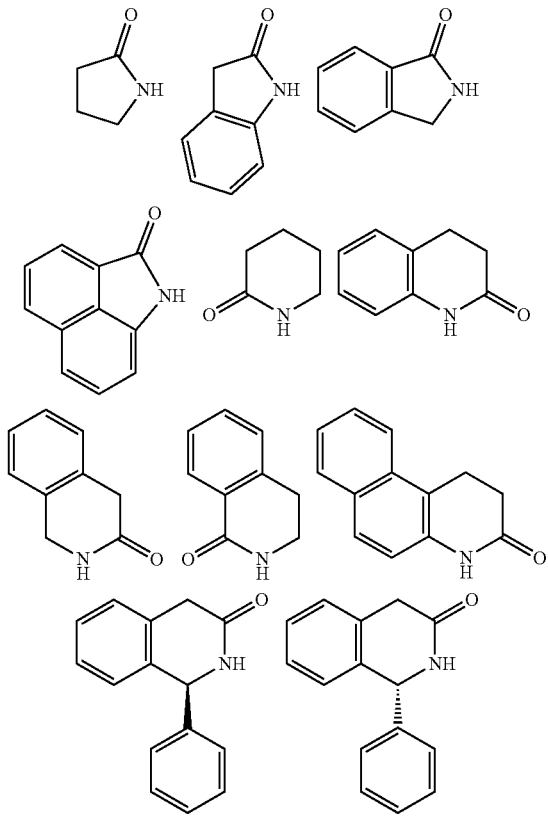

The reaction substrates represented by the formulae (1) to (3) can be represented by, for example, the following formulae (4) to (6), respectively, in one embodiment.

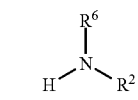
(4)

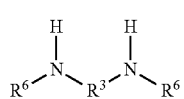
(5)

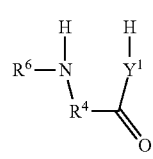
(6)

wherein $R^2$, $R^3$, and $R^4$ each represent a portion other than the reactive group with phosgene of the reaction substrate; $R^6$ is the same as $R^{5a}$ except that $R^6$ is not a hydrogen atom; $R^2$, $R^3$, or $R^4$ and $R^6$ may be bonded to each other; $Y^1$ is NH, and $Y^1$ and $R^4$ and/or $R^6$ may be bonded to each other; and when a plurality of $R^6$'s are present, $R^6$'s may be the same or different.

$R^2$ to $R^4$ can also have various complicated structures according to the reaction substrate as with $R^{1a}$ to $R^{1c}$, but may have a simple structure. Examples of $R^2$ having a simple structure include a monovalent group among the groups exemplified for $R^{1a}$.

Examples of $R^3$ and $R^4$ having a simple structure include a divalent group among the groups exemplified for $R^{1a}$ and $R^{1c}$. One or more examples of the divalent group include an alkylene group having 1 to 10 carbon atoms and optionally having a substituent; a cycloalkanediyl group having 4 to 10 carbon atoms and optionally having a substituent such as a cyclopentane-1,2-diyl group or a cyclohexane-1,2-diyl group (particularly, a cycloalkane-1,2-diyl group); or a divalent aromatic hydrocarbon group having 6 to 10 carbon atoms and optionally having a substituent such as a benzene-1,2-diyl group. The alkylene group can be a group having 1 to 6 carbon atoms such as a methylene group, an ethylene group, a propylene group, a butanediyl group, a pentanediyl group, or a hexanediyl group, and further a group having 1 to 3 carbon atoms. Examples of the substituents of $R^3$ and $R^4$ also include the same groups as those exemplified for $R^{5a}$ to $R^{5b}$.

Examples of the ring formed by bonding $R^6$ and $R^2$ to each other in the formula (4) include the same rings as those in the case of having "$R^{5a}$—N—$R^{1a}$" or "$R^{5a}$—N—$R^{1c}$" in the structural formula as in the formula (1) or the formula (3).

Examples of the ring formed by bonding one of $R^6$'s and $R^3$ to each other in the formula (5) include the following rings.

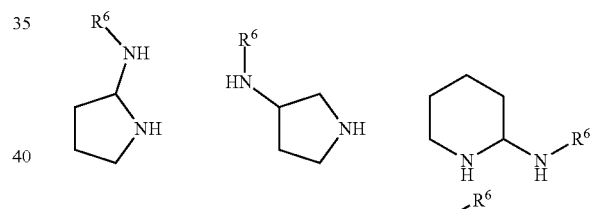

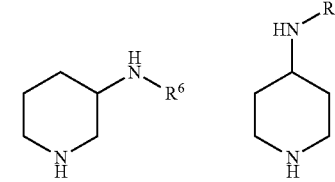

Examples of the ring formed by bonding $Y^1$ and $R^4$ to each other in the formula (6) include the following rings.

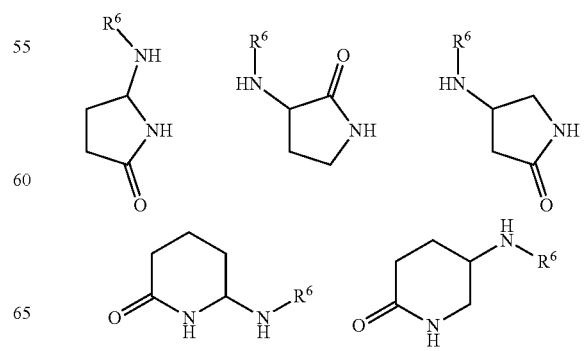

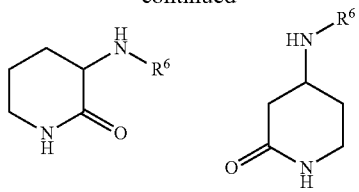

The substrate having a complicated structure among the reaction substrates includes a substrate having a structure represented by the formula (31) such as N-[1-(S)-ethoxycarbonyl-3-phenylpropyl]-L-alanine; and a substrate having a structure represented by the formula (32) such as benzyl 4-[({2S,5R)-5-[benzyloxy)amino]piperidin-2-yl}carbonyl)amino]piperidine-1-carboxylate, tert-butyl 4-[({(2S, 5R)-5-[(benzyloxy)amino]piperidin-2-yl}carbonyl)amino]piperidine-1-carboxylate, benzyl (2S,5R)-5-benzyloxyamino-piperidine-2-carboxylate, methyl (2S,5R)-5-benzyloxyamino-piperidine-2-carboxylate, and (2S,5R)-5-benzyloxyamino-piperidine-2-carboxamide. The substrate having a simple structure among the reaction substrates includes a substrate having a structure represented by the formula (33) such as (S)-1-phenyl-1,2,3,4-tetrahydroisoquinoline, methylamine, ethylamine, propylamine, butylamine, cyclopropylamine, benzylamine, dimethylamine, diethylamine, (R)-1-phenylethylamine, pyrrolidine, piperidine, aniline, acetamide, glycine, L-alanine, L-phenylalanine, glycinamide, L-alanine amide, and L-phenylalaninamide.

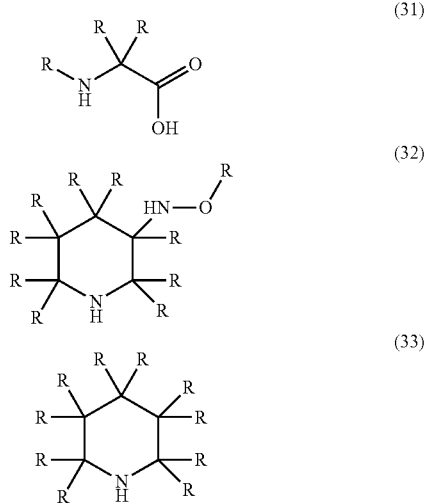

wherein R represents an organic group, and a plurality of R's may be different from each other and become a partial structure of the reaction substrate; and R does not have a reactive group with phosgene.

One or more embodiments may include a reaction substrate that is a substrate having an N-monosubstituted amino group, a substrate having two N-monosubstituted amino groups, a substrate having a cyclized N-monosubstituted amino group, or the like. A substrate having a structure represented by the formula (31), the formula (32), or the formula (33) may also be used.

The reaction substrate may be used as the raw material liquid C in a solvent-free state when used at a temperature equal to or higher than a melting point. However, if necessary, a solution in which the reaction substrate and an organic solvent coexist may be used as the raw material liquid C. The organic solvent can be selected from the same range as the solvents that can be used in the raw material liquid A containing the phosgene alternative reagent.

In one or more embodiments, the amount of the organic solvent in the raw material liquid C is, for example, 50 parts by mass or more, 100 parts by mass or more, or 150 parts by mass or more, and is, for example, 3000 parts by mass or less, 2000 parts by mass or less, or 1000 parts by mass or less, relative to 100 parts by mass of the reaction substrate.

The raw material liquid C may or may not contain a nitrogen-containing organic compound.

In one or more embodiments, a time (reaction time, retention time) during which the mixed solution of the solution containing phosgene prepared in the first flow reactor 21 and the raw material liquid C (reaction substrate) flows in the reactor unit 18 of the second flow reactor 22 may be appropriately set according to the type of the raw material liquid C and the flow velocity at which the mixed solution of the solution containing phosgene and the raw material liquid C flows in the second flow reactor 22, and is, for example, 0.5 seconds or more, 0.6 seconds or more, 0.8 seconds or more, 1.0 second or more, or 1.2 seconds or more, and is, for example, 15 minutes or less, 10 minutes or less, or 5 minutes or less.

In one or more embodiments, the flow velocity at which the raw material liquid C flows in the feeding channel 14 and the flow velocity at which the mixed solution of the solution containing phosgene prepared in the first flow reactor 21 and the raw material liquid C (reaction substrate) flows in the reactor unit 18 of the second flow reactor 22 may be appropriately set according to the type of the raw material liquid C and a retention time in the reactor unit 18. Each flow velocity is, for example, 0.01 mL/min or more, 0.1 mL/min or more, or 0.5 mL/min or more, and is, for example, 5000 mL/min or less, 3000 mL/min or less, or 1000 mL/min (60 L/hour) or less.

In one or more embodiments, the reaction temperature (set temperature of the temperature control device 31) of the solution containing phosgene and the raw material liquid C (reaction substrate) is, for example, −50° C. or higher, −30° C. or higher, or −10° C. or higher, and is, for example, 100° C. or lower, 50° C. or lower, or 25° C. or lower.

The reaction substrate reacts with phosgene in the reactor unit 18, whereby a desired organic compound is obtained. The desired organic compound has a group resulting from conversion of a reactive group with phosgene in the reaction substrate, for example, an N-monosubstituted amino group, an amide group, or a —OC(=O)NH$_2$ group of which a hydrogen atom on a nitrogen atom (N) has been subjected to carbonylation (including chlorocarbonylation). The desired organic compound may have an isocyanate group formed by reaction of the amino group with phosgene.

When the reaction substrates represented by the above formulae (1) to (3) each react with phosgene having the same substance amount as the substance amount of the reactive group, the desired organic compounds represented by the formulae (11) to (15) are synthesized:

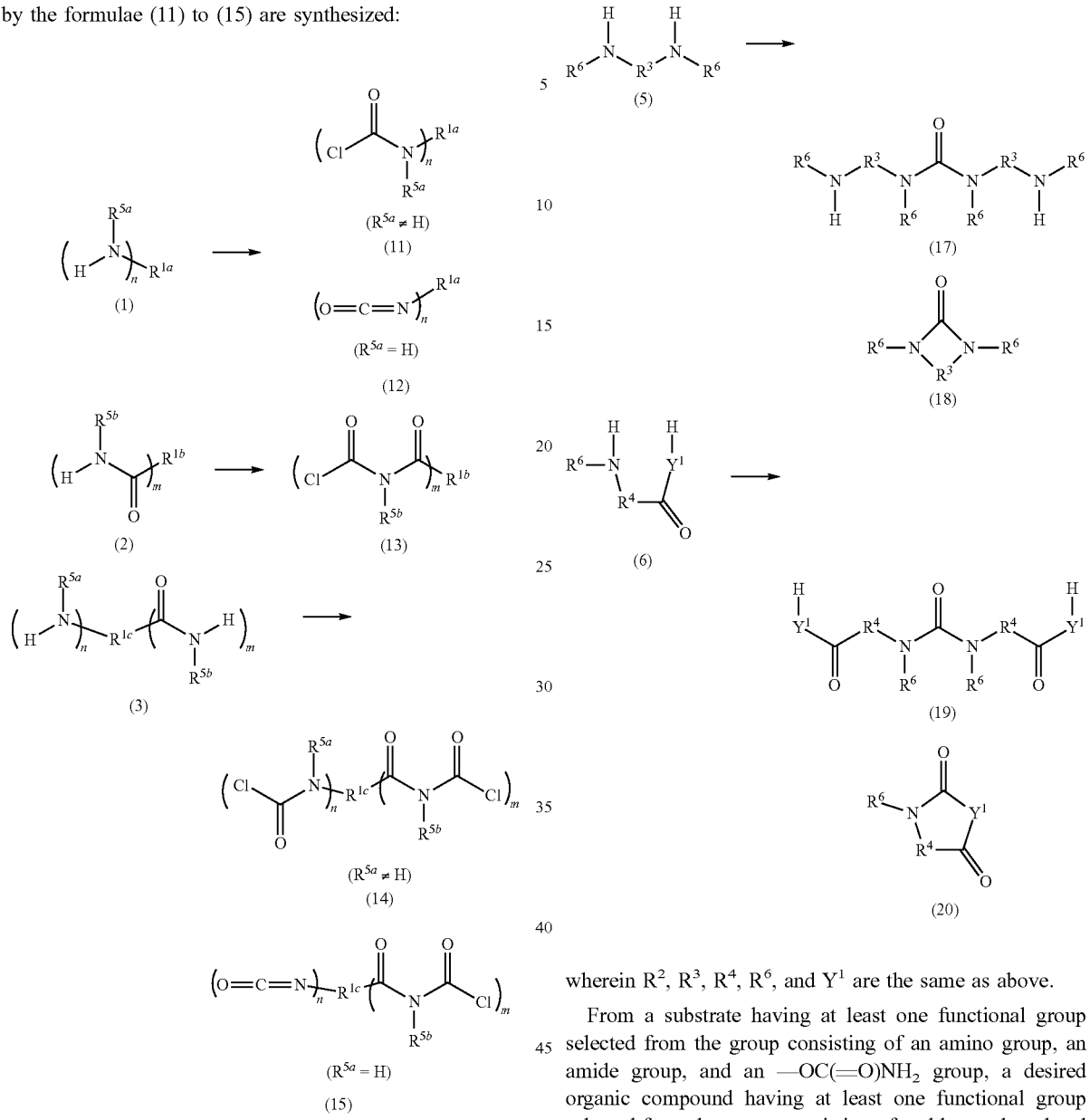

wherein $R^{1a}$, $R^{1b}$, $R^{1c}$, $R^{5a}$, $R^{5b}$, m, and n are the same as above.

When the reaction substrates represented by the above formulae (4) to (6) each react with phosgene having a substance amount half of the substance amount of the reactive group, the desired organic compounds represented by the formulae (16) to (20) are synthesized:

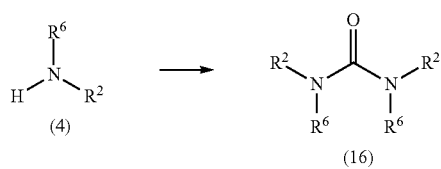

wherein $R^2$, $R^3$, $R^4$, $R^6$, and $Y^1$ are the same as above.

From a substrate having at least one functional group selected from the group consisting of an amino group, an amide group, and an —OC(=O)NH$_2$ group, a desired organic compound having at least one functional group selected from the group consisting of a chlorocarbonylated amino group, a chlorocarbonylated amide group, and a chlorocarbonylated —OC(=O)NH$_2$ group is synthesized.

From a substrate having an N-monosubstituted amino group and a carboxy group, a desired organic compound having a structure of N-carboxyanhydride (NCA) may be synthesized. From a substrate having two N-monosubstituted amino groups, a desired organic compound having a urea structure may be synthesized. From a substrate having a cyclized N-monosubstituted amino group, a desired organic compound having a cyclized N-chlorocarbonyl N-monosubstituted amino group may be synthesized. From the substrates having the structures represented by the formula (31), the formula (32), and the formula (33), desired compounds having the respective structures represented by the formula (41), the formula (42), and the formula (43) are synthesized.

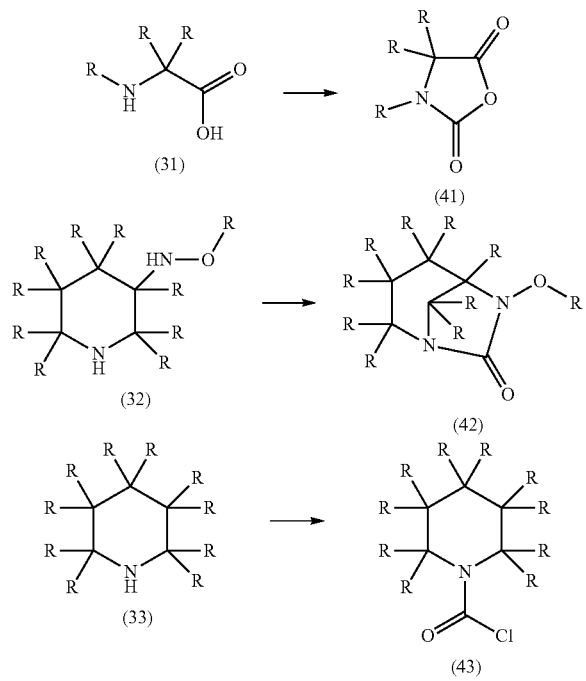

wherein R is the same as above.

As for an impurity that may be by-produced in this process, for example, an impurity having a structure represented by the formula (44) is by-produced from the substrate having the structure represented by the formula (33).

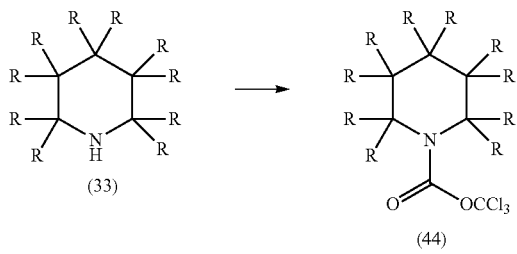

The reaction solution flowing out from the reactor unit 18 is appropriately post-treated as necessary. In the illustrated example, water or an aqueous solution such as water; an acidic aqueous solution containing hydrochloric acid, sulfuric acid, phosphoric acid, acetic acid, citric acid, or the like; and an alkaline aqueous solution containing sodium hydroxide, potassium carbonate, sodium hydrogen carbonate, or the like is placed in a tank 32 for post-treatment, and the reaction solution is fed to the tank 32 to carry out quenching. To the quenched solution, an organic solvent such as ethyl acetate or toluene may be optionally added to extract a desired organic compound. The using amount of water, the acidic aqueous solution, or the alkaline aqueous solution to be used for quenching is not particularly limited. However, the lower limit thereof is generally 0.1 times by weight, 0.5 times by weight, or 1 time by weight, and the upper limit thereof is generally 100 times by weight, 80 times by weight, or 50 times by weight, with respect to the reaction substrate. An organic solvent such as ethyl acetate or toluene may be optionally added, and quenching may be carried out in a two-layer system of water-organic solvent.

In addition, the extract can also be washed with acidic water, inorganic salt water or water as necessary. The reaction solvent and the extraction solvent are distilled away from the resultant extract by an operation such as heating under reduced pressure or the like, whereby a desired product is obtained.

In the reaction apparatus 1 used in one or more embodiments of the present invention, a known device such as a microreactor, a cyclone-shaped reactor, and a laminated microfluidic chip can be appropriately utilized as the flow reactor. A reaction apparatus 2 shown in FIG. 2 is a downsized version of the reaction apparatus 1 shown in FIG. 1, and various devices including these examples can be used as appropriate. In FIG. 2, the components indicated by the same reference numerals as the reference numerals in FIG. 1 are the same components as in FIG. 1. except that they are small in size.

Hereinafter, a modified example of the reaction apparatus 1 will be described with reference to the reaction apparatus 2 of FIG. 2. As liquid transfer means 34a, 34b, and 34c for feeding the raw material liquids to the reactor units 17 and 18, a pump such as a diaphragm pump, a syringe pump, a plunger pump or the like is usually used. In the example of FIG. 2, syringe pumps 35a, 35b, and 35c are used.

In the illustrated examples, a T-shape mixer (including a T-shape tube) is shown as a mixer used as each of the mixing units 15 and 16, but a Y-shape mixer (including a Y-shape tube) can be used as the mixing unit. The mixer may be a static-type mixer, or a helix-type mixer.

Each of the reactor units 17 and 18 in the illustrated examples is not limited to a reactor unit having the coil structure as shown in FIG. 1 and FIG. 2, and may have various structures such as a plate structure in which a micro flow channel is engraved on a plate, a laminated structure in which these plates are stacked, a straight tube structure, or a structure with many bent backs.

In one or more embodiments, the length of each of the reactor units 17 and 18 may be set as appropriate according to the reaction time (retention time), and is, for example, 1 cm or more, 10 cm or more, or 1 m or more. The upper limit of the length of each of the reactor units 17 and 18 is, for example, 500 m or less, 300 m or less, or 100 m or less. The cross-sectional area of each of the flow channels of the mixing units and the reactor units is, for example, 10 μm$^2$ or more, 0.15 mm$^2$ or more, 1 mm$^2$ or more, or 10 mm$^2$ or more. The upper limit of the cross-sectional area of each of the flow channels of the mixing units and the reactor units is, for example, 300 cm$^2$ or less, 70 cm$^2$ or less, or 30 cm$^2$ or less. In particular, the cross-sectional area of each of the flow channels of the mixing units and the reactor units is 1 mm$^2$ or more and 70 cm$^2$ or less, or 0.15 mm$^2$ or more and 30 cm$^2$ or less.

The materials of the mixing units and the reactor units are not particularly limited and may be appropriately selected depending on needs for solvent resistance, pressure resistance, heat resistance, or the like. For example, a metal such as stainless steel, Hastelloy, titanium, copper, nickel and aluminum; a resin such as PEEK resin, silicone resin, and fluororesin; a glass; a ceramics; and SiC can be used.

In one or more embodiments of the present invention, water may or may not coexist as needed. The coexistence of water can more reliably prevent a nitrogen-containing organic compound hydrochloride from precipitating. The nonexistence of water can prevent a side reaction caused by water. When water coexists, the concentration of water in all solvents including solvents contained in other raw material liquids described later (particularly, the concentration of water in the reaction solution of phosgene with a reaction substrate) is, for example, 10 wt % or less, 5 wt % or less, or 1 wt % or less.

A container for quenching the reaction solution is not limited to the tank 32 for post-treatment, and can be selected as appropriate according to the size of the apparatus. For example, a flask 33 as shown in the apparatus of FIG. 2 may be used.

According to the method of one or more embodiments of the present invention using the apparatuses as described above, a desired organic compound can be obtained in a high yield with a small amount of by-product.

The present application claims priority based on Japanese Patent Application No. 2017-173505 filed on Sep. 8, 2017. All the contents described in Japanese Patent Application No. 2017-173505 filed on Sep. 8, 2017 are incorporated herein by reference.

EXAMPLES

Hereinafter, one or more embodiments of the present invention are more specifically described with reference to examples. One or more embodiments of the present invention, however, are not limited by the following examples but can also be absolutely carried out with appropriate changes to the examples within a scope in compliance with the intent described above and later, and all the changes are to be encompassed within a technical scope of one or more embodiments of the present invention.

(1) Production of (S)-1-phenyl-1,2,3,4-tetrahydroisoquinolinecarbonyl Chloride

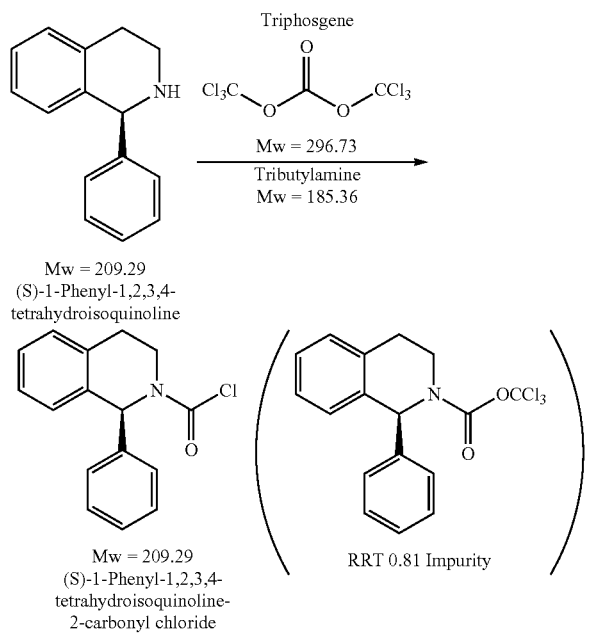

In the following Examples 1 to 6, Comparative Example 1, and Reference Examples 1 and 2, (S)-1-phenyl-1,2,3,4-tetrahydroisoquinolinecarbonyl chloride was produced from (S)-1-phenyl-1,2,3,4-tetrahydroisoquinoline, triphosgene, and tributylamine. The product was quantified by high performance liquid chromatography (HPLC) method to calculate the yield. HPLC conditions were as follows.

Column: CHIRALCEL OD-H (250×4.6 mm) (manufactured by Daicel Corporation)
Mobile phase: hexane/isopropyl alcohol=98/2
Flow rate: 0.7 ml/min
Detection wavelength: UV 220 nm
Column temperature: 35° C.
Retention time: (S)-1-phenyl-1,2,3,4-tetrahydroisoquinolinecarbonyl chloride; 10 minutes
(S)-1-phenyl-1,2,3,4-tetrahydroisoquinoline carboxylic acid trichloromethyl (hereinafter referred to as RRT 0.81 impurity); 8.1 minutes.

Example 1

To 1.70 g of triphosgene, 13.0 g of toluene was added to prepare a homogeneous solution, and the resulting solution was referred to as a raw material liquid A. To 3.20 g of tributylamine, 10.2 g of toluene was added to prepare a homogeneous solution, and the resulting solution was referred to as a raw material liquid B. To 3.00 g of (S)-1-phenyl-1,2,3,4-tetrahydroisoquinoline, 23.8 g of toluene was added to prepare a homogeneous solution, and the resulting solution was referred to as a raw material liquid C. These solutions were reacted using the reaction apparatus 2 shown in FIG. 2 in the following manner.

The raw material liquid A and the raw material liquid B were transferred using syringe pumps (manufactured by YMC Co. Ltd.) 35a and 35b, respectively, at a rate of 1 ml/min and mixed by a T-shape mixer 15, and the resulting mixture was allowed to flow in a retention line 17 for 4 minutes to prepare a toluene solution of phosgene. Next, the raw material liquid C was transferred using a syringe pump (manufactured by YMC Co. Ltd.) 35c at a rate of 2 ml/min and mixed with the toluene solution of phosgene that was continuously flowing (2 ml/min) by another T-shape mixer 16, and the resulting mixture was allowed to flow in a retention line 18 for 2 minutes to perform a reaction. After the syringe containing the raw material liquid A, the raw material liquid B, and the raw material liquid C was emptied, the reagent in the flow channel was washed and flushed with toluene at the same rate. Note that the T-shape mixers 15 and 16 (inner diameter: 2.0 mm, material: polytetrafluoroethylene (PTFE)) and the retention lines 17 and 18 (inner diameter of tube: 2.0 mm, material: polytetrafluoroethylene (PTFE)) were placed in a constant-temperature bath 31 at 10° C. to carry out this examination experiment. The reaction solution was continuously quenched while stirring with 60 g of 2N aqueous hydrochloric acid in a flask 33. After separation, 61.23 g of an organic layer containing 3.52 g of (S)-1-phenyl-1,2,3,4-tetrahydroisoquinolinecarbonyl chloride was obtained (yield: 90%, RRT 0.81 impurity: 0.2 area % vs product area). No crystals precipitated during the reaction, and the reaction solution was a clear solution.

Example 2

To 2.84 g of triphosgene, 7.88 g of toluene was added to prepare a homogeneous solution, and the resulting solution was referred to as a raw material liquid A. To 5.31 g of tributylamine, 3.39 g of toluene was added to prepare a homogeneous solution, and the resulting solution was referred to as a raw material liquid B. To 5.00 g of (S)-1-phenyl-1,2,3,4-tetrahydroisoquinoline, 15.0 g of toluene was added to prepare a homogeneous solution, and the resulting solution was referred to as a raw material liquid C. These solutions were reacted using the reaction apparatus 2 shown in FIG. 2 in the following manner.

The raw material liquid A and the raw material liquid B were transferred using syringe pumps (manufactured by YMC Co. Ltd.) 35a and 35b, respectively, at a rate of 1 ml/min and mixed by a T-shape mixer 15, and the resulting mixture was allowed to flow in a retention line 17 for 5 seconds to prepare a toluene solution of phosgene. Next, the raw material liquid C was transferred using a syringe pump (manufactured by YMC Co. Ltd.) 35c at a rate of 2 ml/min and mixed with the toluene solution of phosgene that was continuously flowing (2 ml/min) by another T-shape mixer 16, and the resulting mixture was allowed to flow in a retention line 18 for 10 seconds to perform a reaction. After the syringe containing the raw material liquid A, the raw material liquid B, and the raw material liquid C was emptied, the reagent in the flow channel was washed and flushed with toluene at the same rate. Note that the T-shape mixers 15 and 16 (inner diameter: 0.5 mm, material: polytetrafluoroethylene (PTFE)) and the retention lines 17 and 18 (inner diameter of tube: 0.5 mm, material: polytetrafluoroethylene (PTFE)) were placed in a constant-temperature bath 31 at 10° C. to carry out this examination experiment. The reaction solution was continuously quenched while stirring with 100 g of 2N aqueous hydrochloric acid in a flask 33. After separation, 40.83 g of an organic layer containing 6.10 g of (S)-1-phenyl-1,2,3,4-tetrahydroisoquinolinecarbonyl chloride was obtained (yield: 94%, RRT 0.81 impurity: not detected). No crystals precipitated during the reaction, and the reaction solution was a clear solution.

Example 3

To 2.84 g of triphosgene, 7.88 g of toluene was added to prepare a homogeneous solution, and the resulting solution was referred to as a raw material liquid A. To 5.31 g of tributylamine, 3.39 g of toluene was added to prepare a homogeneous solution, and the resulting solution was referred to as a raw material liquid B. To 5.00 g of (S)-1-phenyl-1,2,3,4-tetrahydroisoquinoline, 15.0 g of tetrahydrofuran was added to prepare a homogeneous solution, and the resulting solution was referred to as a raw material liquid C. These solutions were reacted using the reaction apparatus 2 shown in FIG. 2 in the following manner.

The raw material liquid A and the raw material liquid B were transferred using syringe pumps (manufactured by YMC Co. Ltd.) 35a and 35b, respectively, at a rate of 1 ml/min and mixed by a T-shape mixer 15, and the resulting mixture was allowed to flow in a retention line 17 for 5 seconds to prepare a toluene solution of phosgene. Next, the raw material liquid C was transferred using a syringe pump (manufactured by YMC Co. Ltd.) 35c at a rate of 2 ml/min and mixed with the toluene solution of phosgene that was continuously flowing (2 ml/min) by another T-shape mixer 16, and the resulting mixture was allowed to flow in a retention line 18 for 10 seconds to perform a reaction. After the syringe containing the raw material liquid A, the raw material liquid B, and the raw material liquid C was emptied, the reagent in the flow channel was washed and flushed with toluene at the same rate. Note that the T-shape mixers 15 and 16 (inner diameter: 0.5 mm, material: polytetrafluoroethylene (PTFE)) and the retention lines 17 and 18 (inner diameter of tube: 0.5 mm, material: polytetrafluoroethylene (PTFE)) were placed in a constant-temperature bath 31 at 10° C. to carry out this examination experiment. The reaction solution was continuously quenched while stirring with 25 g of 2N aqueous hydrochloric acid in a flask 33. After separation, 45.98 g of an organic layer containing 6.20 g of (S)-1-phenyl-1,2,3,4-tetrahydroisoquinolinecarbonyl chloride was obtained (yield: 96%, RRT 0.81 impurity: not detected). No crystals precipitated during the reaction, and the reaction solution was a clear solution.

Example 4

To 28.4 g of triphosgene, 78.0 g of toluene was added to prepare a homogeneous solution, and the resulting solution was referred to as a raw material liquid A. To 53.1 g of tributylamine, 32.5 g of toluene was added to prepare a homogeneous solution, and the resulting solution was referred to as a raw material liquid B. To 50.0 g of (S)-1-phenyl-1,2,3,4-tetrahydroisoquinoline, 150.0 g of tetrahydrofuran was added to prepare a homogeneous solution, and the resulting solution was referred to as a raw material liquid C. These solutions were reacted using the reaction apparatus 1 shown in FIG. 1 in the following manner.

The raw material liquid A and the raw material liquid B were transferred using diaphragm pumps (manufactured by KNF Co. Ltd.) 34a and 34b, respectively, at a rate of 39.5 ml/min and mixed by a T-shape mixer 15, and the resulting mixture was allowed to flow in a retention line 17 for 5 seconds to prepare a toluene solution of phosgene. Next, the raw material liquid C was transferred using a diaphragm pump (manufactured by KNF Co. Ltd.) 34c at a rate of 79.0 ml/min and mixed with the toluene solution of phosgene that was continuously flowing (79.0 ml/min) by another T-shape mixer 16, and the resulting mixture was allowed to flow in a retention line 18 for 10 seconds to perform a reaction. After the bottles containing the raw material liquid A, the raw material liquid B, and the raw material liquid C was emptied, the reagent in the flow channel was washed and flushed with toluene at the same rate. Note that the T-shape mixers 5 and 16 (inner diameter: 2.4 mm, material: stainless (SUS304)) and the retention lines 17 and 18 (inner diameter: 3.0 mm, outer diameter: 4.0 mm, material: polytetrafluoroethylene (PTFE)) were placed in a constant-temperature bath 31 at 10° C. to carry out this examination experiment. The reaction solution was continuously quenched while stirring with 250.0 g of 2N aqueous hydrochloric acid in a flask 32. After separation, 443.3 g of an organic layer containing 63.6 g of (S)-1-phenyl-1,2,3,4-tetrahydroisoquinolinecarbonyl chloride was obtained (yield: 98%, RRT 0.81 impurity: 0 area % vs product area). No crystals precipitated during the reaction, and the reaction solution was a clear solution.

Example 5

To 28.4 g of triphosgene, 78.0 g of toluene was added to prepare a homogeneous solution, and the resulting solution was referred to as a raw material liquid A. To 53.1 g of tributylamine, 32.5 g of toluene was added to prepare a homogeneous solution, and the resulting solution was referred to as a raw material liquid B. To 50.0 g of (S)-1-phenyl-1,2,3,4-tetrahydroisoquinoline, 150.0 g of tetrahydrofuran was added to prepare a homogeneous solution, and the resulting solution was referred to as a raw material liquid C. These solutions were reacted using the reaction apparatus 1 shown in FIG. 1 in the following manner.

The raw material liquid A and the raw material liquid B were transferred using diaphragm pumps (manufactured by KNF Co. Ltd.) 34a and 34b, respectively, at a rate of 39.5 ml/min and mixed by a T-shape mixer 15, and the resulting mixture was allowed to flow in a retention line 17 for 5 seconds to prepare a toluene solution of phosgene. Next, the raw material liquid C was transferred using a diaphragm pump (manufactured by KNF Co. Ltd.) 34c at a rate of 79.0 ml/min and mixed with the toluene solution of phosgene that was continuously flowing (79.0 ml/min) by another T-shape mixer 16, and the resulting mixture was allowed to flow in a retention line 18 for 10 seconds to perform a reaction. After the bottles containing the raw material liquid A, the raw material liquid B, and the raw material liquid C was emptied, the reagent in the flow channel was washed and flushed with toluene at the same rate. Note that the T-shape mixers 15 and 16 (inner diameter: 2.4 mm, material: stainless (SUS304)) and the retention lines 17 and 18 (inner diameter: 2.18 mm, outer diameter: ⅛ inch (about 3.18 mm), material: stainless (SUS304)) were placed in a constant-temperature bath 31 at 10° C. to carry out this examination experiment. The reaction solution was continuously quenched while stirring with 250.0 g of 2N aqueous hydrochloric acid in a flask 32. After separation, 465.4 g of an organic layer containing 63.1 g of (S)-1-phenyl-1,2,3,4-tetrahydroisoquinolinecarbonyl chloride was obtained (yield: 98%, RRT 0.81 impurity: 0 area % vs product area). No crystals precipitated during the reaction, and the reaction solution was a clear solution.

Example 6

To 28.4 g of triphosgene, 78.0 g of toluene was added to prepare a homogeneous solution, and the resulting solution was referred to as a raw material liquid A. To 53.1 g of tributylamine, 32.5 g of toluene was added to prepare a homogeneous solution, and the resulting solution was referred to as a raw material liquid B. To 50.0 g of (S)-1-phenyl-1,2,3,4-tetrahydroisoquinoline, 150.0 g of tetrahydrofuran was added to prepare a homogeneous solution, and the resulting solution was referred to as a raw material liquid C. These solutions were reacted using the reaction apparatus 1 shown in FIG. 1 in the following manner.

The raw material liquid A and the raw material liquid B were transferred using diaphragm pumps (manufactured by KNF Co. Ltd.) 34a and 34b, respectively, at a rate of 39.5 ml/min and mixed by a T-shape mixer 15, and the resulting mixture was allowed to flow in a retention line 17 for 5 seconds to prepare a toluene solution of phosgene. Next, the raw material liquid C was transferred using a diaphragm pump (manufactured by KNF Co. Ltd.) 34c—at a rate of 79.0 ml/min and mixed with the toluene solution of phosgene that was continuously flowing (79.0 ml/min) by another T-shape mixer 16, and the resulting mixture was allowed to flow in a retention line 18 for 10 seconds to perform a reaction. After the bottles containing the raw material liquid A, the raw material liquid B, and the raw material liquid C was emptied, the reagent in the flow channel was washed and flushed with toluene at the same rate. Note that the T-shape mixers 15 and 16 (inner diameter: 4.8 mm, material: stainless (SUS304)) and the retention lines 17 and 18 (inner diameter of tube: 4.0 mm, outer diameter of tube: 6.0 mm, material: stainless (SUS304)) were placed in a constant-temperature bath 31 at 10° C. to carry out this examination experiment. The reaction solution was continuously quenched while stirring with 250.0 g of 2N aqueous hydrochloric acid in a flask 32. After separation, 457.4 g of an organic layer containing 63.9 g of (S)-1-phenyl-1,2,3,4-tetrahydroisoquinolinecarbonyl chloride was obtained (yield: 97%, RRT 0.81 impurity: 0 area % vs product area). No crystals precipitated during the reaction, and the reaction solution was a clear solution.

Reference Example 1 (Examination 1 of Required Retention Time)

To 7.37 g of triphosgene, 49.4 g of toluene was added to prepare a homogeneous solution, and the resulting solution was referred to as a raw material liquid A. Next, to 13.81 g of tributylamine, 42.9 g of toluene was added to prepare a homogeneous solution, and the resulting solution was referred to as a raw material liquid B (corresponding to a raw material liquid D in FIG. 3). These solutions were reacted using a reaction apparatus 3 shown in FIG. 3 in the following manner. Note that the reaction apparatus 3 is the same as the reaction apparatus 2 of FIG. 2 except that the second flow reactor 22 is not provided. The same components are indicated by the same reference numerals, and the descriptions thereof are omitted. The outlet of the reaction tube and a React IR15 were connected, and the reaction conversion rate was calculated by means of inline analysis.

The raw material liquid A and the raw material liquid B (corresponding to a raw material liquid D in FIG. 3) were transferred using syringe pumps (manufactured by YMC Co. Ltd.) 35a and 35d and mixed by a T-shape mixer 15 (inner diameter: 0.5 mm, material: polytetrafluoroethylene (PTFE)), and the resulting mixture was allowed to flow in a retention line 17 (inner diameter: 0.5 mm, material: polytetrafluoroethylene (PTFE)) to prepare a toluene solution of phosgene. Note that the T-shape mixers 15 and the retention lines 17 were placed in a constant-temperature bath 31 at 10° C. to carry out this examination experiment. The retention time was adjusted to 0.5 to 4.9 seconds by changing the flow rate of each flow channel in a range of 1.0 to 9.0 ml/min. The conversion rate from triphosgene to phosgene at each retention time is shown in Table 1.

<Characteristic peak>triphosgene: 1836 $cm^{-1}$, phosgene: 1809 $cm^{-1}$

TABLE 1

| retention time (sec) | 0.5 | 0.6 | 0.7 | 0.8 | 1.0 | 1.6 | 4.9 |
|---|---|---|---|---|---|---|---|
| conversion rate (%) | 64 | 87 | 94 | 97 | 100 | 100 | 100 |

Reference Example 2 (Examination 2 of Required Retention Time)

To 7.37 g of triphosgene, 49.4 g of toluene was added to prepare a homogeneous solution, and the resulting solution was referred to as a raw material liquid A. To 13.81 g of tributylamine, 42.9 g of toluene was added to prepare a homogeneous solution, and the resulting solution was referred to as a raw material liquid B. To 13.00 g of (S)-1-phenyl-1,2,3,4-tetrahydroisoquinoline, 101.4 g of toluene was added to prepare a homogeneous solution, and the resulting solution was referred to as a raw material liquid C. These solutions were reacted using the reaction apparatus 2 shown in FIG. 2 in the following manner. The outlet of the reaction tube and a React IR15 were connected, and the reaction conversion rate was calculated by means of inline analysis.

The raw material liquid A and the raw material liquid B were transferred using syringe pumps (manufactured by YMC Co. Ltd.) 35a and 35b, respectively, at a rate of 1 ml/min and mixed by a T-shape mixer 15 (inner diameter: 0.5 mm, material: polytetrafluoroethylene (PTFE)), and the resulting mixture was allowed to flow in a retention line 17 (inner diameter: 0.5 mm, material: polytetrafluoroethylene (PTFE)) for 5 seconds to prepare a toluene solution of phosgene. Next, the raw material liquid C was transferred using a syringe pump (manufactured by YMC Co. Ltd.) 35c at a rate of 2 ml/min and mixed with the toluene solution of phosgene that was continuously flowing (2 ml/min) by another T-shape mixer 16 (inner diameter: 0.5 mm, material:

polytetrafluoroethylene (PTFE)), and the resulting mixture was allowed to flow in a retention line 18 (inner diameter: 0.5 mm, material: polytetrafluoroethylene (PTFE)) to perform a reaction. Note that the T-shape mixers 15 and 16 and the retention lines 17 and 18 were placed in a constant-temperature bath 31 at 10° C. to carry out this examination experiment. The retention time was adjusted to 0.6 to 8.5 seconds by changing the length of the retention line 18 in a range of 19 to 289 cm. The yield of the product ((S)-1-phenyl-1,2,3,4-tetrahydroisoquinolinecarbonyl chloride) at each retention time is shown in Table 2.

TABLE 2

| retention time (sec) | 0.6 | 1.2 | 8.5 |
|---|---|---|---|
| yield (%) | 95 | 100 | 100 |

Comparative Example 1

To 283.7 mg of triphosgene, 4.25 g of toluene was added to prepare a homogeneous solution, and the resulting solution was referred to as a raw material liquid A. To 500 mg of (S)-1-phenyl-1,2,3,4-tetrahydroisoquinoline, 3.21 g of toluene and 531.6 mg of tributylamine were added to prepare a homogeneous solution, and the resulting solution was referred to as a raw material liquid D. These solutions were reacted using the reaction apparatus 3 shown in FIG. 3 in the following manner.

The T-shape mixer 15 (inner diameter: 0.5 mm, material: polytetrafluoroethylene (PTFE)) and the retention line 17 (inner diameter of tube: 1.0 mm, material: polytetrafluoroethylene (PTFE)) were placed in the constant-temperature bath 31 at 10° C. Then, the raw material liquid A and the raw material liquid D were transferred using the syringe pumps (manufactured by YMC Co. Ltd.) 35a and 35d, respectively, at a rate of 0.5 ml/min and mixed by a micromixer 15, and the resulting mixture was allowed to flow in the retention line 17 for 2 minutes to perform a reaction. After the syringe containing the raw material liquid A and the raw material liquid D was emptied, the reagent in the flow channel was washed and flushed with toluene at the same rate. The reaction solution was continuously quenched while stirring with 10 g of 2N aqueous hydrochloric acid in the flask 33. After separation, 12.71 g of an organic layer containing 272.7 mg of (S)-1-phenyl-1,2,3,4-tetrahydroisoquinolinecarbonyl chloride was obtained (yield: 42%, RRT 0.81 impurity: 72 area % vs product area). No crystals precipitated during the reaction, and the reaction solution was a clear solution.

(2) Production of N-[1-(S)-ethoxycarbonyl-3-phenylpropyl]-L-alanyl-N-carboxyanhydride

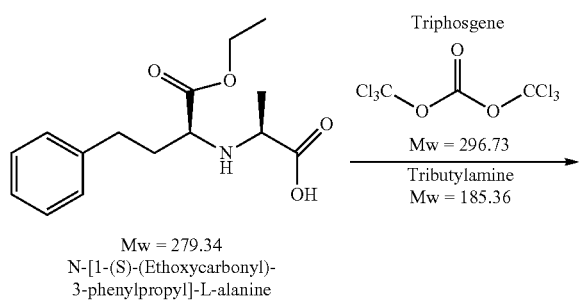

Mw = 279.34
N-[1-(S)-(Ethoxycarbonyl)-3-phenylpropyl]-L-alanine

Triphosgene
Mw = 296.73
Tributylamine
Mw = 185.36

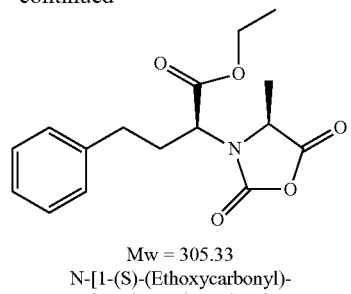

Mw = 305.33
N-[1-(S)-(Ethoxycarbonyl)-3-phenylpropyl]-L-alanyl-N-carboxyanhydride In the following Example 7 and Comparative Example 2, N-[1-(S)-ethoxycarbonyl-3-phenylpropyl]-L-alanyl-N-carboxyanhydride was produced from N-[1-(S)-ethoxycarbonyl-3-phenylpropyl]-L-alanine and triphosgene. The product was quantified by HPLC method to calculate the yield. HPLC conditions were as follows.

Column: CHIRALPAC IA (250×4.6 mm)
Mobile phase: hexane/ethanol=90/10
Flow rate: 0.8 ml/min
Detection wavelength: UV 220 nm
Column temperature: 35° C.
Retention time: N-[1-(S)-ethoxycarbonyl-3-phenylpropyl]-L-alanyl-N-carboxyanhydride; 10 minutes Example 7

To 0.64 g of triphosgene, 3.38 g of toluene was added to prepare a homogeneous solution, and the resulting solution was referred to as a raw material liquid A. To 0.40 g of tributylamine, 3.62 g of toluene was added to prepare a homogeneous solution, and the resulting solution was referred to as a raw material liquid B. To 1.50 g of N-[1-(S)-ethoxycarbonyl-3-phenylpropyl]-L-alanine and 1.09 g of tributylamine, 13.50 g of tetrahydrofuran was added to prepare a homogeneous solution, and the resulting solution was referred to as a raw material liquid C. These solutions were reacted using the reaction apparatus 1 shown in FIG. 1 in the following manner.

The raw material liquid A and the raw material liquid B were transferred using diaphragm pumps (manufactured by KNF Co. Ltd.) 35a and 35b, respectively, at a rate of 1.0 ml/min and mixed by a T-shape mixer 15, and the resulting mixture was allowed to flow in a retention line 17 for 1 minutes to prepare a toluene solution of phosgene. Next, the raw material liquid C was transferred using a diaphragm pump (manufactured by KNF Co. Ltd.) 35c at a rate of 2.0 ml/min and mixed with the toluene solution of phosgene that was continuously flowing (2.0 ml/min) by another T-shape mixer 16, and the resulting mixture was allowed to flow in a retention line 18 for 3 minutes to perform a reaction. After the bottles containing the raw material liquid A, the raw material liquid B, and the raw material liquid C was emptied, the reagent in the flow channel was washed and flushed with toluene at the same rate. Note that the T-shape mixers 15 and 16 (inner diameter: 0.5 mm, material: polytetrafluoroethylene (PTFE)) and the retention lines 17 and 18 (inner diameter of tube: 2.0 mm, material: polytetrafluoroethylene (PTFE)) were placed in a constant-temperature bath 31 at 35° C. to carry out this examination experiment. The reaction solution was continuously quenched while stirring with 75.0 g of 18% phosphoric acid aqueous solution in a flask 32. After separation, 100.14 g of an organic layer containing 1.31 g of N-[1-(S)-ethoxycarbonyl-3-phenylpropyl]-L-alanyl-N-carboxyanhydride was obtained (yield: 80%). No crystals precipitated during the reaction, and the reaction solution was a clear solution.

Comparative Example 2

To 0.64 g of triphosgene, 15.50 g of toluene was added to prepare a homogeneous solution, and the resulting solution was referred to as a raw material liquid A. To 1.50 g of N-[1-(S)-ethoxycarbonyl-3-phenylpropyl]-L-alanine, 13.50 g of tetrahydrofuran and 1.09 g of tributylamine were added to prepare a homogeneous solution, and the resulting solution was referred to as a raw material liquid D. These solutions were reacted using the reaction apparatus 3 shown in FIG. 3 in the following manner.

The T-shape mixer 15 (inner diameter: 0.5 mm, material: polytetrafluoroethylene (PTFE)) and the retention line 17 (inner diameter of tube: 2 mm, material: polytetrafluoroethylene (PTFE)) were placed in the constant-temperature bath 31 at 35° C. Then, the raw material liquid A and the raw material liquid D were transferred using the syringe pumps (manufactured by YMC Co. Ltd.) 35a and 35d, respectively, at a rate of 2 ml/min and mixed by a micromixer 15, and the resulting mixture was allowed to flow in the retention line 17 for 4 minutes to perform a reaction. After the syringe containing the raw material liquid A and the raw material liquid D was emptied, the reagent in the flow channel was washed and flushed with toluene at the same rate. The reaction solution was continuously quenched while stirring with 75.0 g of 18% phosphoric acid aqueous solution in the flask 33. After separation, 45.00 g of an organic layer containing 1.13 g of N-[1-(S)-ethoxycarbonyl-3-phenylpropyl]-L-alanyl-N-carboxyanhydride was obtained (yield: 69%). No crystals precipitated during the reaction, and the reaction solution was a clear solution.

Although the disclosure has been described with respect to only a limited number of embodiments, those skilled in the art, having benefit of this disclosure, will appreciate that various other embodiments may be devised without departing from the scope of one or more embodiments of the present invention. Accordingly, the scope of one or more embodiments of the invention should be limited only by the attached claims.

REFERENCE SIGNS LIST 11, 12, 13, 14: feeding channel
15, 16: mixing unit
17, 18: reactor unit
21, 22: flow reactor

What is claimed is:

1. A process for producing an organic compound using an apparatus comprising:
 a first flow reactor for a first reaction in which a raw material liquid A and a raw material liquid B are introduced from separate feeding channels, mixed in a first mixing unit, and then reacted in a first reactor unit, and
 a second flow reactor for a second reaction in which a first reaction solution discharged from the first flow reactor for the first reaction and a raw material liquid C are introduced from separate feeding channels, mixed in a second mixing unit, and then reacted in a second reactor unit,
 wherein the raw material liquid A is a solution in which triphosgene and/or diphosgene is dissolved,
 wherein the raw material liquid B is a nitrogen-containing organic compound not including an amino group, an amino group comprising one substituent on N, an amido group, an amido group comprising one substituent on N, a —OC(=O)NH$_2$, and a —OC(=O)NH$_2$ comprising one substituent on N, or a solution of the nitrogen-containing organic compound,
 wherein the raw material liquid C is a reaction substrate having at least one functional group capable of reacting with phosgene, the functional group being selected from the group consisting of an amino group, an amino group comprising one substituent on N, an amido group, an amido group comprising one substituent on N, a —OC(=O)NH$_2$, and a —OC(=O)NH$_2$ comprising one substituent on N, or a solution containing the reaction substrate, and
 wherein a product of the first reaction is phosgene.

2. The process according to claim 1,
 wherein the organic compound produced is a compound having at least one functional group selected from the group consisting of a chlorocarbonylated amino group, a chlorocarbonylated amino group comprising one substituent on N, a chlorocarbonylated amide group, a chlorocarbonylated amide group comprising one substituent on N, a chlorocarbonylated —OC(=O)NH$_2$, and a chlorocarbonylated —OC(=O)NH$_2$ group comprising one substituent on N, a compound having a structure of N-carboxyanhydride, or a compound having a isocyanate or urea structure.

3. The process according to claim 1,
 wherein the nitrogen-containing organic compound not including an amino group, an amino group comprising one substituent on N, an amido group, an amido group comprising one substituent on N, a —OC(=O)NH$_2$, and a —OC(=O)NH$_2$ comprising one substituent on N is a trialkylamine having 9 to 40 carbon atoms, and
 wherein the solution in which triphosgene and/or diphosgene is dissolved contains an organic solvent.

4. The process according to claim 1,
 wherein a flow channel to discharge the first reaction solution from the first reactor unit of the first flow reactor for the first reaction is directly connected to the mixing unit of the second flow reactor for the second reaction.

5. The process according to claim 1,
 wherein the first reactor unit has a cross-sectional area of 0.15 mm$^2$ to 30 cm$^2$.

6. The process according to claim 1,
 wherein the second reactor unit has a cross-sectional area of 0.15 mm$^2$ to 30 cm$^2$.

* * * * *